(12) United States Patent
Walker et al.

(10) Patent No.: US 8,945,186 B2
(45) Date of Patent: Feb. 3, 2015

(54) MULTI-AXIAL SPINAL CROSS CONNECTING DEVICE

(75) Inventors: Clint Walker, Frisco, TX (US); Stephen Termyna, Boonton, NJ (US); John Lovell, North Bergen, NJ (US)

(73) Assignee: Blackstone Medical, Inc., Lewisville, TX (US)

( * ) Notice: Subject to any disclaimer, the term of this patent is extended or adjusted under 35 U.S.C. 154(b) by 0 days.

(21) Appl. No.: 13/341,636

(22) Filed: Dec. 30, 2011

(65) Prior Publication Data

US 2013/0172934 A1    Jul. 4, 2013

(51) Int. Cl.
*A61B 17/70* (2006.01)

(52) U.S. Cl.
USPC ............................ 606/250; 606/251; 606/252

(58) Field of Classification Search
USPC .......................... 606/246, 250–253, 260, 278
See application file for complete search history.

(56) References Cited

U.S. PATENT DOCUMENTS

| | | | |
|---|---|---|---|
| 4,046,344 A | 9/1977 | Scanlan | |
| 5,520,689 A | 5/1996 | Schlapfer et al. | |
| 5,527,310 A | 6/1996 | Cole et al. | |
| 5,669,910 A | 9/1997 | Korhonen et al. | |
| 6,217,578 B1 | 4/2001 | Crozet et al. | |
| 6,264,658 B1 | 7/2001 | Lee et al. | |
| 6,302,882 B1 | 10/2001 | Lin et al. | |
| 6,309,390 B1 | 10/2001 | Le Couedic et al. | |
| 6,540,748 B2 | 4/2003 | Lombardo | |
| 6,547,790 B2 | 4/2003 | Harkey, III et al. | |
| 6,595,992 B1 | 7/2003 | Wagner et al. | |
| 6,699,248 B2 | 3/2004 | Jackson | |
| 6,752,807 B2 | 6/2004 | Lin et al. | |
| 6,783,526 B1 | 8/2004 | Lin et al. | |
| 6,866,664 B2 | 3/2005 | Schar et al. | |
| 7,066,938 B2 | 6/2006 | Slivka et al. | |
| 7,160,301 B2 | 1/2007 | Cordaro | |
| 7,232,441 B2 | 6/2007 | Altarac et al. | |
| 7,270,665 B2 | 9/2007 | Morrison et al. | |

(Continued)

FOREIGN PATENT DOCUMENTS

EP          0572790 B1     2/1996
WO      2007041085 A1     4/2007

OTHER PUBLICATIONS

International Search Report & Written Opinion, PCT/US2012/072110, dated Mar. 15, 2013, 9 pages.

(Continued)

*Primary Examiner* — Mary Hoffman
*Assistant Examiner* — Christina Negrellirodrigue
(74) *Attorney, Agent, or Firm* — Baker & McKenzie LLP

(57) ABSTRACT

A cross connecting device suitable for connecting first and second spinal fixation devices comprises a fixable pivot junction, first and second connection members, and first and second clamps. The fixable pivot junction includes a pivotable joint that is pivotable about a pivot point. The fixable pivot junction also includes a collar configured for fixating the pivot junction. The first and second connection members are connected by the fixable pivot junction such that the fixable pivot junction allows the first and second connection members to be repositioned relative to each other. The first and second clamps are connected to respective ones of the first and second connection members at distal ends of the connection members relative to the fixable pivot junction. The first and second clamps allow the cross connecting device to be clamped on to spinal fixation devices, such as pedicle screws or hooks.

16 Claims, 11 Drawing Sheets

(56) References Cited

U.S. PATENT DOCUMENTS

| | | |
|---|---|---|
| 7,344,537 B1 | 3/2008 | Mueller |
| 7,481,827 B2 | 1/2009 | Ryan et al. |
| 7,621,942 B2 | 11/2009 | Piehl |
| 7,645,294 B2 | 1/2010 | Kalfas et al. |
| 7,695,500 B2 | 4/2010 | Markworth |
| 7,717,939 B2 | 5/2010 | Ludwig et al. |
| 7,918,876 B2 | 4/2011 | Mueller et al. |
| 8,025,679 B2 | 9/2011 | Nichols et al. |
| 8,361,117 B2 * | 1/2013 | Michielli et al. ............... 606/253 |
| 2003/0045874 A1 | 3/2003 | Thomas, Jr. |
| 2003/0114853 A1 | 6/2003 | Burgess et al. |
| 2003/0130661 A1 | 7/2003 | Osman |
| 2004/0133203 A1 | 7/2004 | Young et al. |
| 2005/0090821 A1 | 4/2005 | Berrevoets et al. |
| 2005/0228326 A1 | 10/2005 | Kalfas et al. |
| 2005/0228377 A1 | 10/2005 | Chao et al. |
| 2006/0058789 A1 | 3/2006 | Kim et al. |
| 2006/0064093 A1 | 3/2006 | Thramann et al. |
| 2006/0235392 A1 | 10/2006 | Hammer et al. |
| 2006/0271051 A1 * | 11/2006 | Berrevoets et al. ............ 606/61 |
| 2007/0016197 A1 | 1/2007 | Woods et al. |
| 2007/0118121 A1 | 5/2007 | Purcell et al. |
| 2007/0213723 A1 | 9/2007 | Markworth et al. |
| 2008/0021456 A1 | 1/2008 | Gupta et al. |
| 2008/0086134 A1 | 4/2008 | Butler et al. |
| 2008/0091205 A1 | 4/2008 | Kuiper et al. |
| 2008/0109039 A1 | 5/2008 | Michielli et al. |
| 2008/0125781 A1 | 5/2008 | Hoffman et al. |
| 2008/0147123 A1 | 6/2008 | Schermerhorn |
| 2008/0172093 A1 | 7/2008 | Nilsson |
| 2008/0177314 A1 | 7/2008 | Lemoine |
| 2008/0177315 A1 | 7/2008 | Usher |
| 2009/0210007 A1 | 8/2009 | Levy et al. |
| 2009/0270924 A1 | 10/2009 | Wing et al. |
| 2009/0312801 A1 | 12/2009 | Lemoine et al. |
| 2010/0010541 A1 | 1/2010 | Boomer et al. |
| 2010/0094345 A1 * | 4/2010 | Saidha et al. ............... 606/250 |
| 2010/0152776 A1 | 6/2010 | Keyer et al. |
| 2010/0204733 A1 | 8/2010 | Rathbun et al. |
| 2010/0222779 A1 | 9/2010 | Ziemek et al. |
| 2010/0256681 A1 | 10/2010 | Hammer et al. |
| 2010/0324557 A1 | 12/2010 | Cheema et al. |
| 2011/0190824 A1 | 8/2011 | Gephart et al. |

OTHER PUBLICATIONS

International Search Report and Written Opinion, PCT/US2012/072107, 9 pages, dated Mar. 1, 2013.

International Search Report and Written Opinion, PCT/US2012/032805, dated Aug. 3, 2012, 8 pages.

U.S. Notice of Allowance, U.S. Appl. No. 13/341,587, dated Jun. 13, 2013, 10 pages.

* cited by examiner

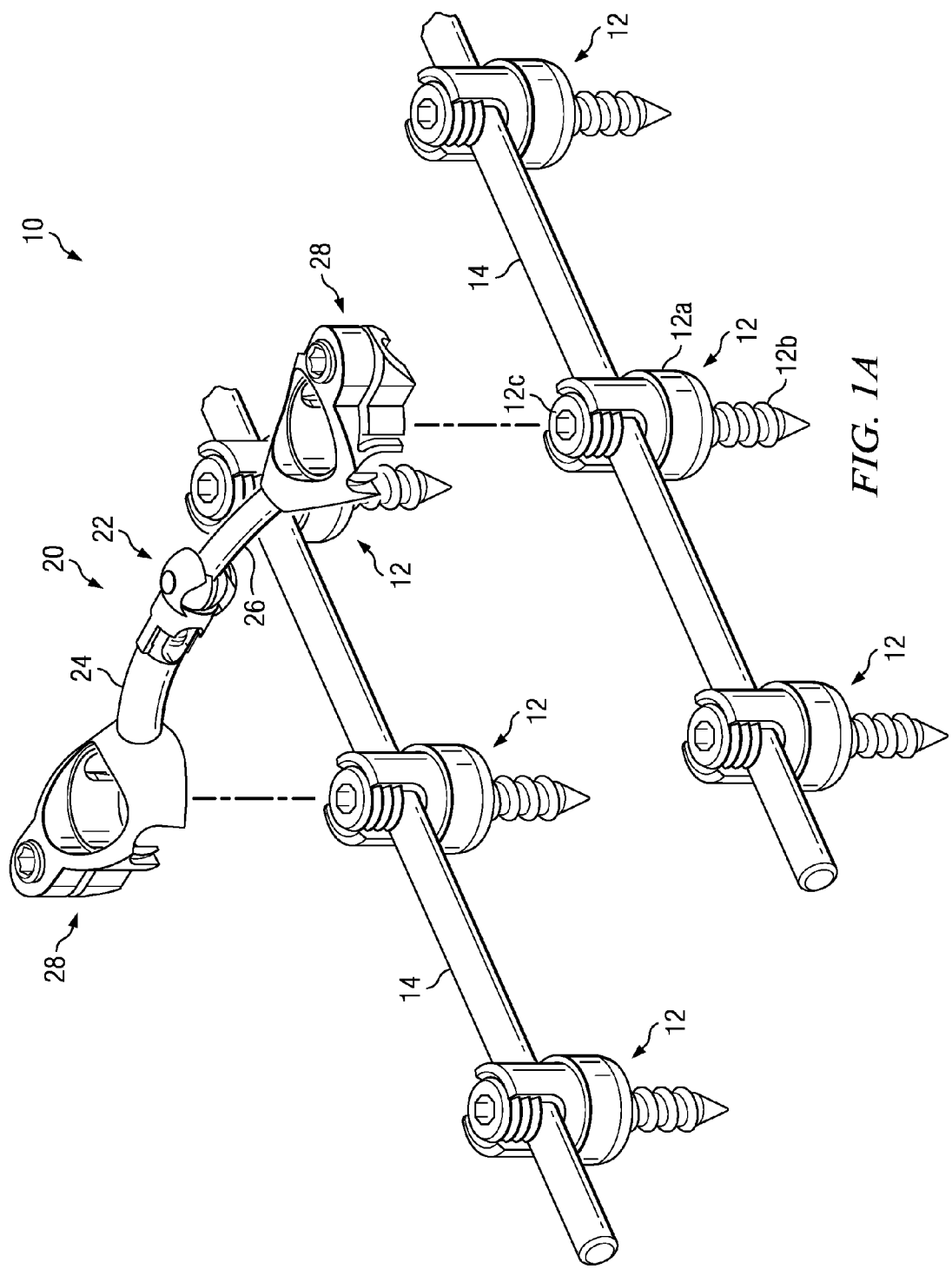

MULTI-AXIAL SPINAL CROSS CONNECTING DEVICE

BACKGROUND

1. Technical Field

The present application relates to connection systems for spinal fixation devices, including cross connecting devices for spinal fixation bone anchors such as bone screws and hooks.

2. Related Art

The bones and connective tissue of an adult human spinal column includes more than twenty vertebrae coupled sequentially to one another by a tri joint complex. The complex includes an anterior disc and two posterior facet joints. The anterior discs of adjacent bones are cushioned by cartilage spacers referred to as intervertebral discs. The vertebrae are each anatomically categorized into one of four classifications: cervical, thoracic, lumbar, and sacral. The cervical portion of the spine, which comprises the top of the spine up to the base of the skull, includes the first seven vertebrae. The intermediate twelve vertebrae are thoracic vertebrae, and connect to the lower spine comprising five lumbar vertebrae. The base of the spine includes the sacral bones (including the coccyx).

The spinal column is highly complex in that it includes over twenty vertebrae coupled to one another for housing and protecting critical elements of the nervous system. These elements of the nervous system have seemingly innumerable peripheral nerves and circulatory bodies in close proximity to each other. Despite its complexity, the spine is a highly flexible structure, capable of a high degree of curvature and twisting in many different directions.

However, genetic or developmental irregularities, trauma, chronic stress, tumors and disease can result in spinal pathologies that either limit this range of motion, or threaten the critical elements of the nervous system protected by the spinal column. A variety of systems have been disclosed in the art which provide some degree of immobilization of the spine by implanting artificial assemblies in or onto the spinal column. These assemblies include anterior, posterior, and lateral assemblies. Lateral and anterior assemblies can be coupled to the anterior portion of the spine, typically between vertebral bodies. Posterior spinal fixation systems generally include a pair of rods, which can be aligned along an axis to which the bones are to be disposed, and which are then attached to the spinal column by spinal fixation bone anchors, such as pedicle hooks and/or pedicle screws. Hooks can be coupled to the lamina or attached to transverse processes, while screws can be inserted through pedicles. In order to provide enhanced torsional rigidity, these structures can include cross-connecting devices for coupling the rods together in a direction that is generally transverse with respect to the axis of the rods. These cross-connecting devices can be coupled directly to the rods themselves, or can be attached to the bone anchors.

A number of improvements to prior cross-connecting devices are desirable. For example, it is desirable to provide cross-connecting devices that are highly adjustable, for example both length-wise and angularly in several degrees of freedom.

SUMMARY

Spinal fixation devices, cross connecting devices for spinal fixation devices, and components thereof, including fixable pivot junctions and clamps for cross connecting devices, are described herein.

According to one aspect of the present disclosure, a cross connecting device suitable for connecting first and second spinal fixation devices comprises a fixable pivot junction, first and second connection members, and first and second clamps. The fixable pivot junction can include a collar and a pivotable joint. The pivotable joint can be pivotable about a pivot point, and the collar can be configured for fixating the pivot junction. The first and second connection members can be connected by the fixable pivot junction such that the fixable pivot junction can allow the first and second connection members to be repositioned relative to each other. The first and second clamps can be connected to respective ones of the first and second connection members at distal ends of the connection members relative to the fixable pivot junction.

The collar can be slidable between an unlocking position and a locking position. The illustrated embodiments show a locking position closer to a pivot point of the pivotable joint than the unlocking position. However, in alternative embodiments, the locking position can be further from the pivot point of the pivotable joint than the unlocking position, for example by reversing and/or relocating tapered surfaces so that compression occurs as the collar is moved away from the pivotable joint.

The pivotable joint can comprise a tapered interface and a split pivot element. The tapered interface can be fixed to the first connection member. The tapered interface can be configured for applying a compressive load to the split pivot element and the second connection member while the slidable collar is in the locking position. The tapered interface can comprise opposing solid faces, or can comprise a plurality of slits surrounding the split pivot element.

The collar can comprise first and second tabs for preventing the movement of the collar from the locking position to the unlocking position.

The first and second clamps can be configured to be connected to respective ones of the first and second spinal fixation devices. The first and second clamps can each include a locking member, such as a set screw, pin, or other device, that can be used to tighten the clamp onto a spinal fixation device. The clamps can each include a socket for receiving the locking member, where the socket includes a top hole and a bottom hole, the bottom hole being misaligned with the top hole. The locking members can each include a tapered end, which can pass through the misaligned bottom hole as the set screw is driven into the socket, thereby urging the misaligned bottom hole to align with the top hole as the locking member is driven into the socket. The clamp can be configured to tighten onto a spinal fixation device as the misaligned bottom hole is aligned with the top hole by the locking member.

The clamps can each include an outer housing and an inner housing. The outer housing and the inner housing can be angularly adjustable relative to each other, for example along at least one degree of freedom. The outer housing and the inner housing can each include one or more channels that allow for expansion and/or compression of the housing. The channels can include a transverse channel region for controlling the expansion/compression direction of the housing.

The fixable pivot junction can allow the first and second connection members to be translationally, rotationally, and/or angularly repositioned relative to each other.

According to another aspect of the present disclosure, a fixable pivot junction for connecting first and second connection members of a cross connecting device is disclosed for a cross connecting device that is suitable for connecting first and second spinal fixation devices. The fixable pivot junction can comprise a collar and a pivotable joint. The collar can be slidable between an unlocking position and a locking position. The pivotable joint can be pivotable about a pivot point while the collar is in the unlocking position, and the collar can be configured for fixating the pivot junction while the collar is in the locking position. The pivotable joint can comprise a tapered interface connected to a first connection member, and a split pivot element configured for receiving a second connection member.

In some embodiments, the locking position can be closer to a pivot point of the pivotable joint than the unlocking position, while in other embodiments the locking position can be further from the pivot point of the pivotable joint than the unlocking position. In some embodiments, the tapered interface can be configured for applying a compressive load to the split pivot element and the second connection member while the slidable collar is in the locking position. The tapered interface can comprise opposing solid faces or a plurality of slits surrounding the split pivot element. The collar can further comprise one or more tabs for preventing the movement of the collar from the locking position to the unlocking position. The fixable pivot junction can allow the first and second connection members to be translationally, rotationally, and/or angularly repositioned relative to each other. These and other features, aspects, and embodiments of the invention are described below in the section entitled "Detailed Description."

BRIEF DESCRIPTION OF THE DRAWINGS

Features, aspects, and embodiments of the inventions are described in conjunction with the attached drawings, in which:

FIGS. 1A and 1B show a spinal fixation system having a cross connecting device according to the present disclosure;

DETAILED DESCRIPTION

Figure 1B:
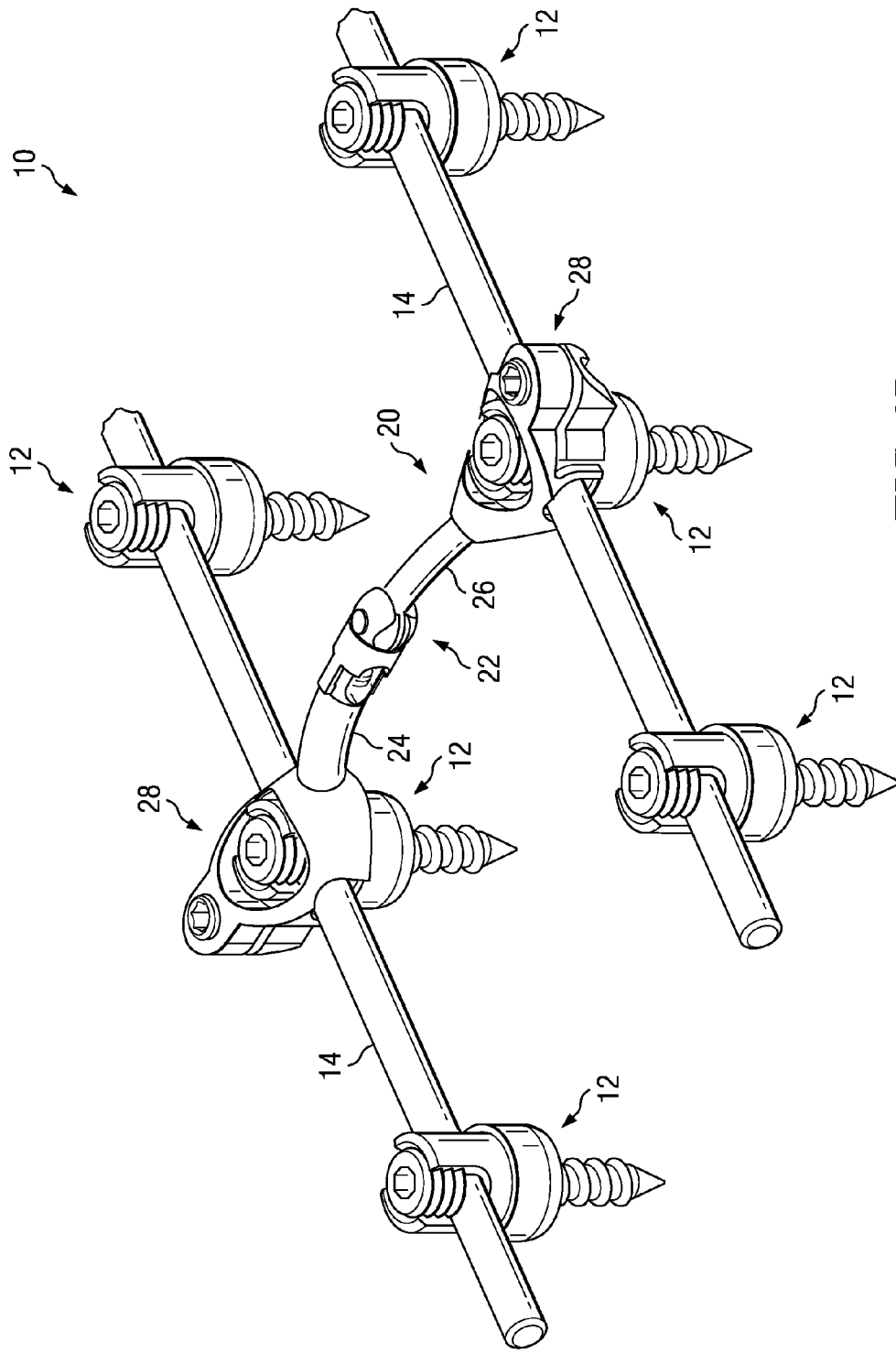

FIGS. 1A and 1B show a spinal fixation system 10 that includes a plurality of spinal fixation devices 12, a pair of rods 14, and a cross connecting device 20.

The cross connecting device 20 can be used with a wide variety of fixation devices. However, for the sake of clarity, an example of spinal fixation devices 12 are shown and described as spinal fixation devices 12. In this example, the spinal fixation devices 12 can include pedicle screws as shown, and can include other types of bone anchors, including hooks. Each fixation device 12 can include, for example, a body 12*a*, a shank 12*b*, and a set screw 12*c*. There are various known body styles, including the open style shown. Alternative styles include closed, reduction, and offset body styles. The shank 12*b* can be cannulated or non-cannulated. The shank 12*b* can be monoaxial or mutliaxial relative to the body 12*a*. Each shank 12*b* can include a single-lead thread as shown, or can include multiple-lead threads, where there are two or more threads that wind along the shank, usually equally spaced apart from each other. Instead of a shank 12*b*, one or more of the bodies 12*a* can include, or be attached to, a hook that can be attached to vertebrae, for example in the cervical area where vertebrae are small.

Once the spinal fixation devices 12 are secured to bone, the rods 14 can be placed along the bodies 12*a* and secured in place by the set screws 12*c*. Then, once the rods 14 are secured to the spinal fixation devices 12, the cross connecting device 20 can be placed over bodies 12*a* of a pair of spinal fixation devices 12 as shown in FIGS. 1A and 1B.

The cross connecting device 20 includes a fixable pivot junction 22, a first connection member 24, a second connection member 26, and clamps 28. The cross connecting device 20 can be lengthwise and angularly adjusted, thereby accommodating for translational, rotational, and angular misalignments between the connected spinal fixation devices 12. More specifically, the first and second connection members 24 and 26 are connected by the fixable pivot junction 22 such that the fixable pivot junction 22 allows the first and second connection members 24 and 26 to be translationally, rotationally, and angularly repositioned relative to each other. Once desired adjustments are made, the fixable pivot junction 22 can be locked, and the clamps 28 can be secured to the rods 14 as described in greater detail below.

Figure 2A:
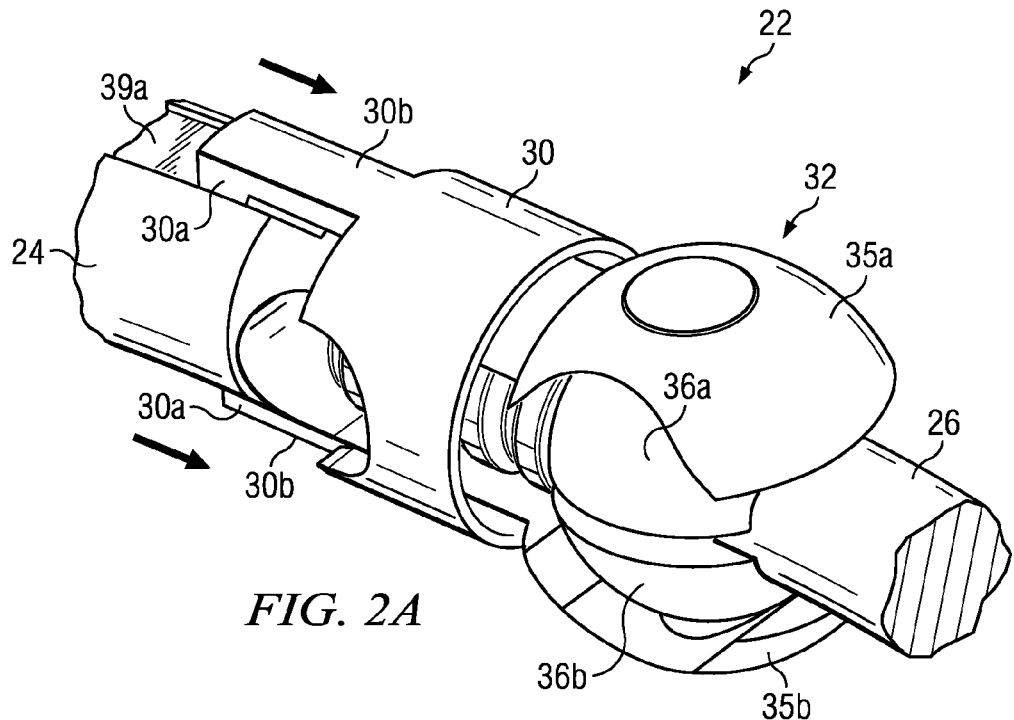
FIGS. 2A-2C show a first embodiment a fixable pivot junction suitable for use with the cross connecting device shown in FIGS. 1A and 1B.
Figure 2B:
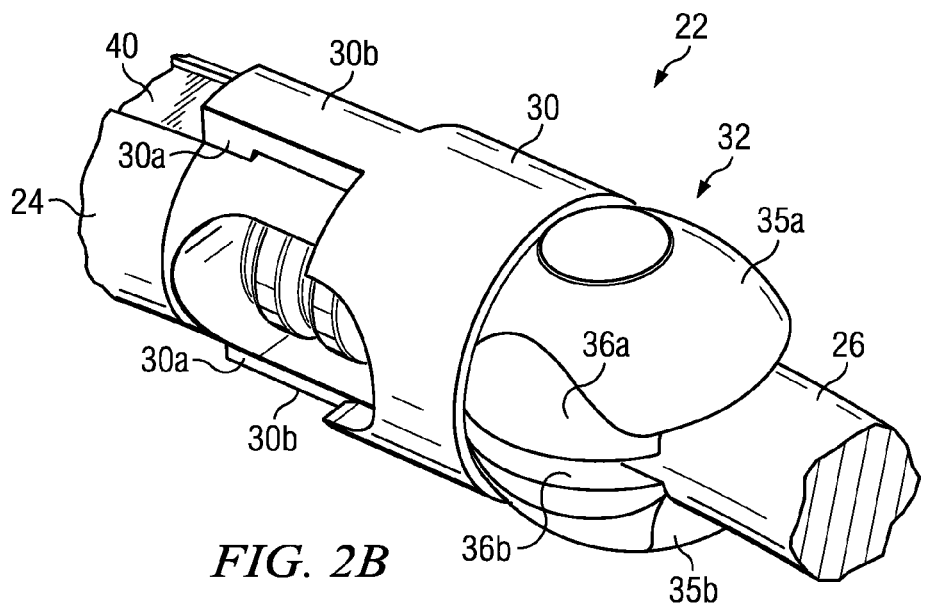
Figure 2C:
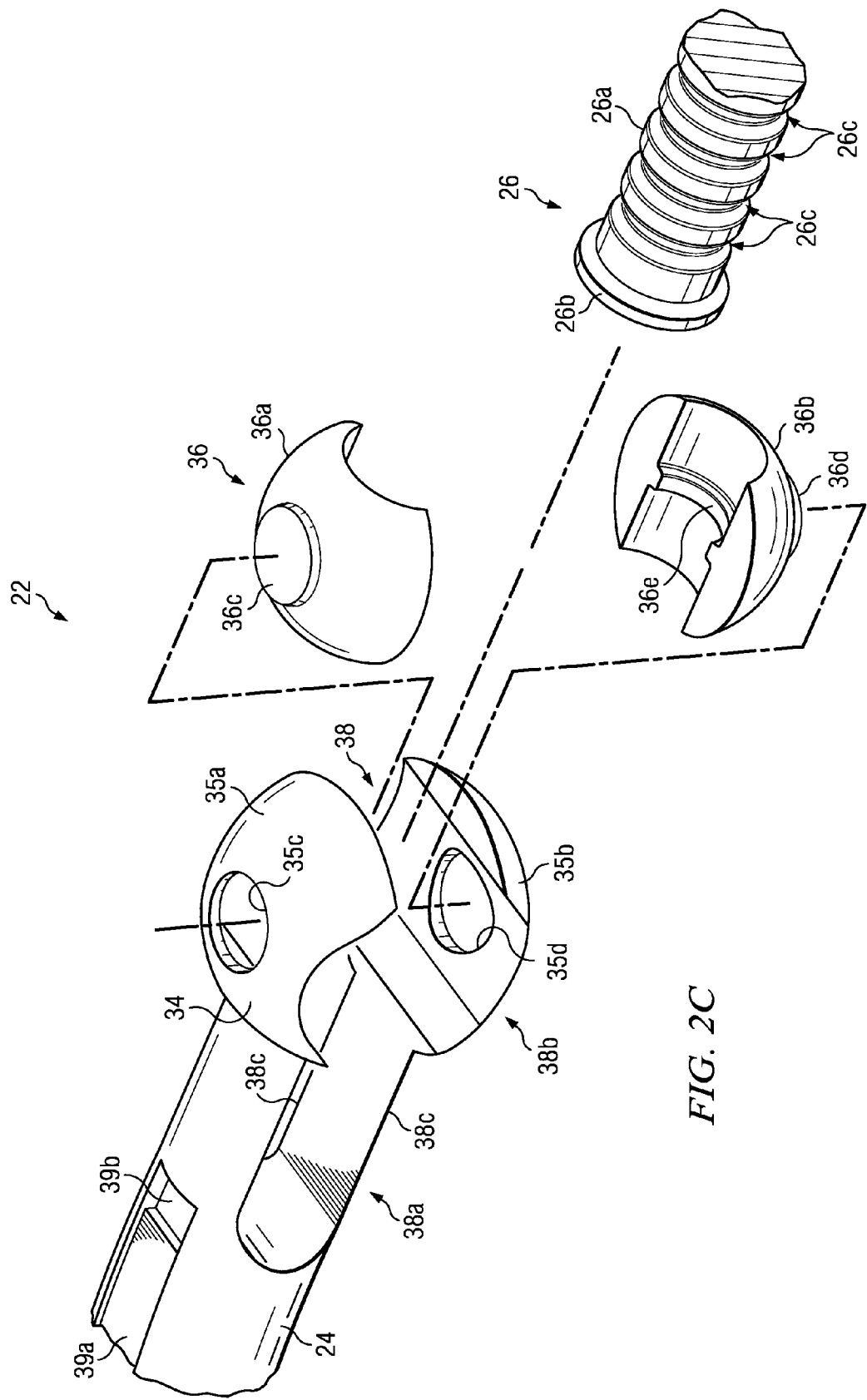

Referring next to FIGS. 2A-2C, the fixable pivot junction 22 includes a slidable collar 30 and a pivotable joint 32. The pivotable joint 32 can be locked or unlocked depending on the position of the collar 30. The collar 30 is configured for fixating the pivot junction 22. The collar 30 is slidable between an unlocking position, which is shown in FIG. 2A, and a locking position, which is shown in FIG. 2B. Thus, in FIG. 2A, the pivotable joint 32 is unlocked, and in FIG. 2B the pivotable joint 32 is locked. When the pivotable joint 32 is unlocked, the pivotable joint 32 is pivotable about a pivot point approximately central thereto. In alternative embodiments, the fixable pivot junction 22 can be alternatively arranged such that the locking position of the collar 30 is further from the pivot point of the pivotable joint 32 than the unlocking position, for example by reversing and/or relocating tapered surfaces (tapered interface 34) so that compression occurs as the collar 30 is moved away from the pivotable joint 32.

FIG. 2C shows an exploded view of the pivotable joint 32. The collar 30 is not shown in FIG. 2C in order to allow for an improved view of the pivotable joint 32. The pivotable joint 32 comprises a tapered interface 34 and a split pivot element 36. The tapered interface 34 is fixed to the first connection member 24. The tapered interface 34 includes opposing faces 35*a* and 35*b* at least partially surrounding the split pivot element 36.

The split pivot element 36 can be, for example, a split spherical element having upper and lower halves 36*a* and 36*b*. Alternatively, the split pivot element 36 can have only a single split. For example, the split pivot element 36 can be a spherical element having a single split. The split in the split pivot element 36 allows the split pivot element 36 to be compressed onto a straight portion 26*a* of the second connection member 26. Also, each of the upper and lower halves 36*a* and 36b have a respective tooth 36e that is configured to mate with the channels 26c in the connection member 26.

A mating feature can be provided for helping to position the upper and lower halves 36a and 36b of the split pivot element 36 within the tapered interface 34. For example, in the illustrated embodiment, each of the upper and lower halves 36a and 36b includes a respective boss 36c, 36d. The bosses 36c and 36d are sized and shaped so as to mate with respective through-holes 35c and 35d that extend through respective faces 35a and 35b of the tapered interface 34.

While the pivotable joint 32 is unlocked, the split pivot element 36 is free to rotate within the tapered interface 34, and the straight portion 26a of the second connection member 26 is free to slide through the split pivot element 36 (between the upper and lower halves 36a and 36b). The second connection member 26 can also rotate axially between the upper and lower halves 36a and 36b of the split pivot element while the pivotable joint 32 is unlocked.

While the pivotable joint 32 is locked, the tapered interface 34 is configured for applying a compressive load to the split pivot element 36 and the second connection member 26. The compressive load is sufficient to prevent the split pivot element 36 from rotating within the tapered interface 34, and to also prevent the second connection member 26 from sliding between the upper and lower halves 36a and 36b of the split pivot element 36. The second connection member 26 is also prevented from rotating axially between the upper and lower halves 36a and 36b of the split pivot element while the pivotable joint 32 is locked. In some embodiments, the second connection member 26 can have a protruding shoulder or tab feature, such as tab 26b, to prevent separation, i.e., to prevent the second connection member 26 from being withdrawn through the split pivot element 36.

The first connection member 24 includes a cavity 38 for receiving the straight portion 26a of the second connection member 26 and for receiving the split pivot element 36. The cavity 38 includes a first cavity portion 38a into which the straight portion 26a of the second connection member 26 can translate. The cavity 38 also includes a second cavity portion 38b for receiving and supporting the split pivot element 36, thereby allowing for multi-axial movement of the second connection member 26 relative to the first connection member 24. The cavity 38 further includes openings 38c in opposing sides of the first connection member 24. The openings 38c allow portions of the straight portion 26a that extend beyond the split pivot element 36 and into the first cavity portion 38a to be moved more freely, thereby allowing the for an increased range of motion between the first and second connection members 24 and 26.

The collar 30 can include one or more tabs 30a for preventing the movement of the collar 30 from the locking position shown in FIG. 2B back to the unlocking position shown in FIG. 2A. The tabs 30a travel along respective guiding recesses 39a, which are formed along the first connection member 24. The tabs 30a reside on a distal end of a trailing resilient arm 30b, which urges the tabs 30a toward the first connection member 24. Thus, once the collar 30 is moved to the locking position shown in FIG. 2B, the tabs 30a snap into corresponding locking recesses 39b, thereby locking the position of the collar 30.

Figure 3A:
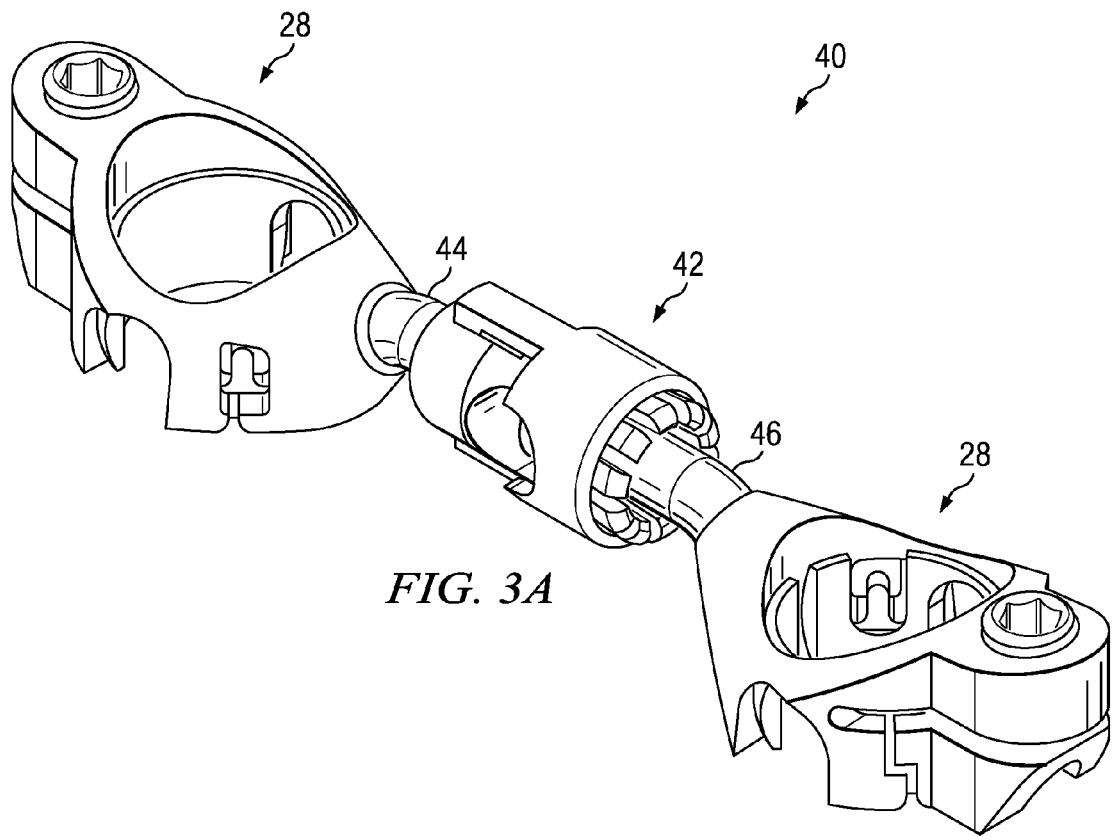
FIGS. 3A and 3B show a cross connecting device having a second embodiment of a fixable pivot junction suitable for use with the spinal fixation system shown in FIGS. 1A and 1B.
Figure 3B:
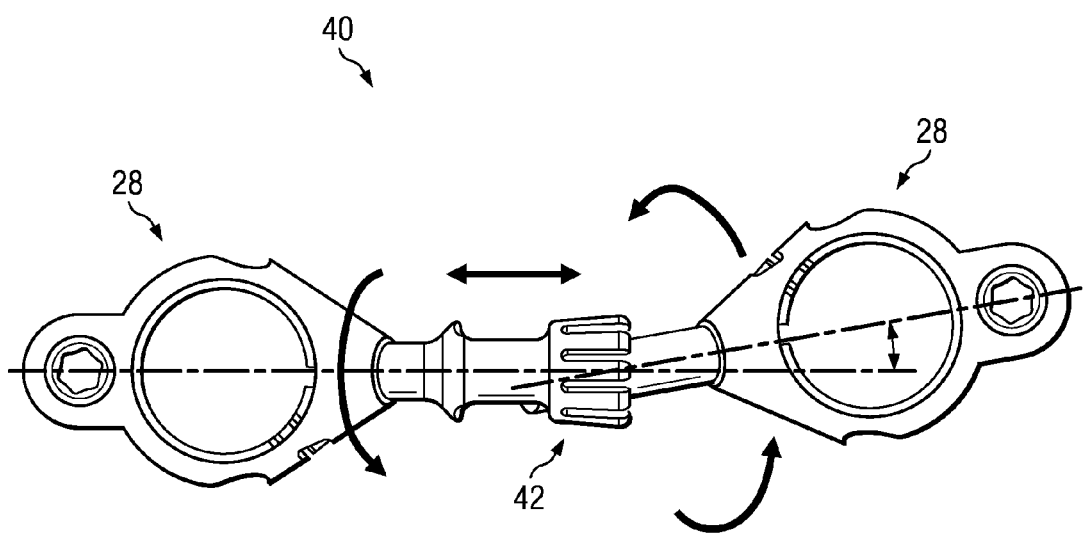

Turning next to FIGS. 3A and 3B, an alternative embodiment of the cross connecting device is shown as cross connecting device 40. The cross connecting device 40 can replace the cross connecting device 20 in the spinal fixation system 10 shown in FIGS. 1A and 1B. The cross connecting device 40 includes a fixable pivot junction 42, a first connection member 44, and a second connection member 46. The cross connecting device 40 can also include the clamps 28. The cross connecting device 40 can be lengthwise and angularly adjusted, thereby accommodating for translational, rotational, and angular misalignments between the connected spinal fixation devices 12. More specifically, the first and second connection members 44 and 46 are connected by the fixable pivot junction 42 such that the fixable pivot junction 42 allows the first and second connection members 44 and 46 to be translationally, rotationally, and angularly repositioned relative to each other, as illustrated by FIG. 3B.

Figure 4A:
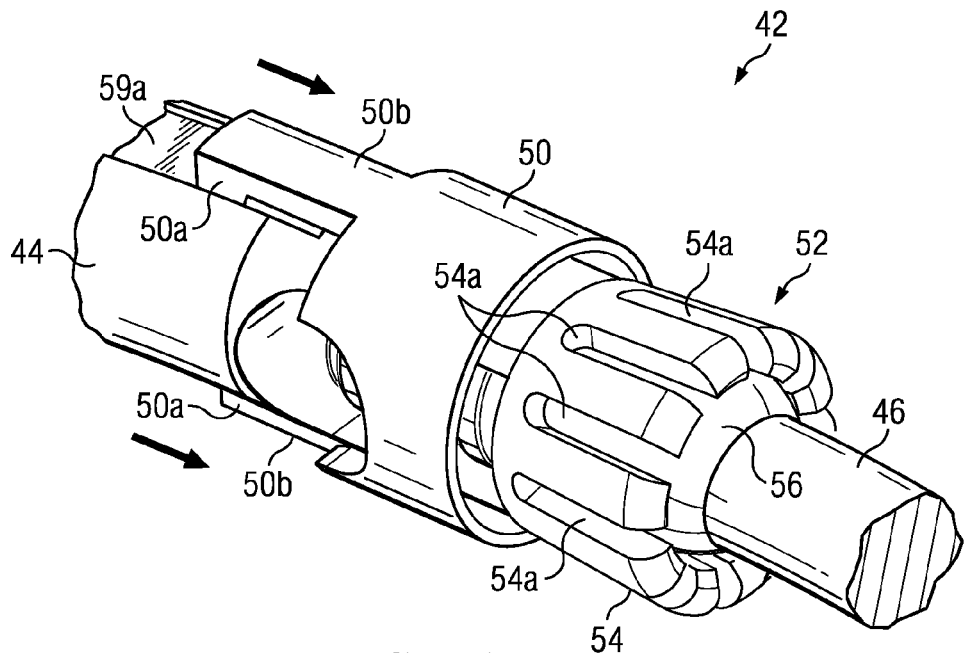
FIGS. 4A-4D show the second embodiment of the fixable pivot junction shown in FIGS. 3A and 3B.
Figure 4B:
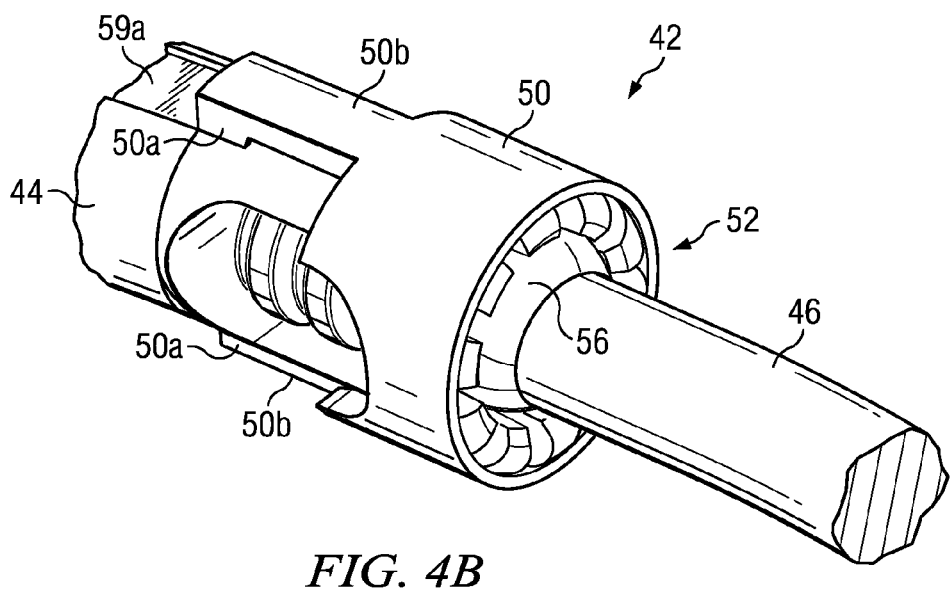

Referring next to FIGS. 4A-4D, the fixable pivot junction 42 includes a slidable collar 50 and a pivotable joint 52. The pivotable joint 52 can be locked or unlocked depending on the position of the collar 50. The collar 50 is configured for fixating the pivot junction 42. The collar 50 is slidable between an unlocking position, which is shown in FIG. 4A, and a locking position, which is shown in FIG. 4B. Thus, in FIG. 4A, the pivotable joint 52 is unlocked, and in FIG. 4B the pivotable joint 52 is locked. When the pivotable joint 52 is unlocked, the pivotable joint 52 is pivotable about a pivot point approximately central thereto.

Figure 4C:
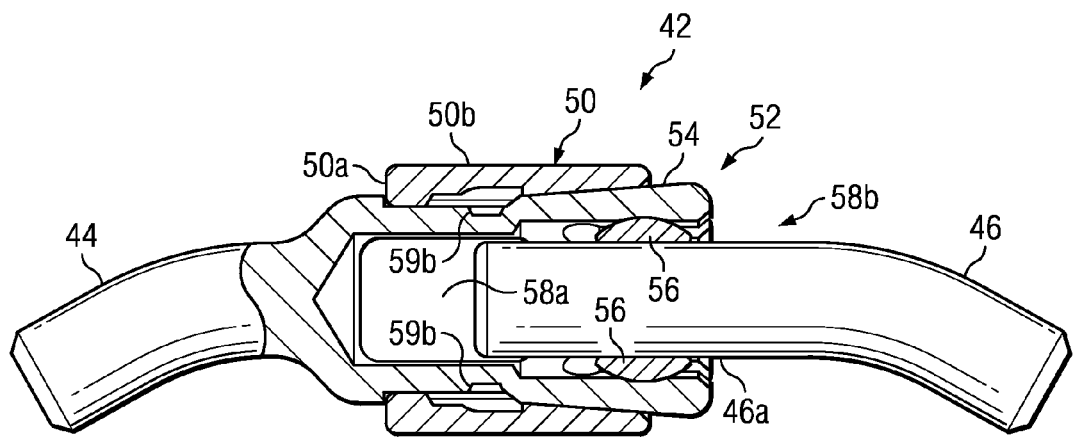
Figure 4D:
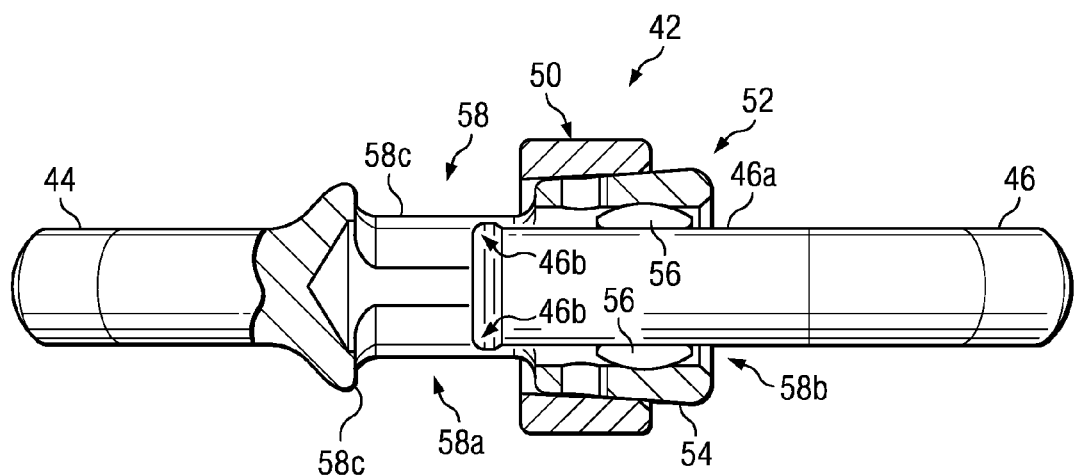

FIGS. 4C and 4D show respective cross-sectional views of the pivotable joint 52. The pivotable joint 52 comprises a tapered interface 54 and a split pivot element 56. The tapered interface 54 is fixed to the first connection member 44. The tapered interface 54 includes a plurality of slits 54a to form a collet-like device surrounding the split pivot element 56.

The split pivot element 56 can be, for example, a split spherical element identical to the split pivot element 36 shown in FIG. 2C having upper and lower halves, or, alternatively, the split pivot element 56 can have only a single split. For example, the split pivot element 56 can be a spherical element having a single split. Also, in some embodiments, the split pivot element 56 can include any number of relief cuts or channels in order to allow for sufficient contact with the connection member 46. The split in the split pivot element 56 allows the split pivot element 56 to be compressed onto a straight portion 46a of the second connection member 46.

While the pivotable joint 52 is unlocked, the split pivot element 56 is free to rotate within the tapered interface 54, and the straight portion 46a of the second connection member 46 is free to slide through the split pivot element 56. The second connection member 46 can also rotate axially through the split pivot element 56 while the pivotable joint 52 is unlocked.

While the pivotable joint 52 is locked, the tapered interface 54 is configured for applying a compressive load to the split pivot element 56 and the second connection member 46. The compressive load is sufficient to prevent the split pivot element 56 from rotating within the tapered interface 54, and to also prevent the second connection member 46 from sliding through the split pivot element 56. The second connection member 46 is also prevented from rotating axially through the split pivot element 56 while the pivotable joint 52 is locked. In some embodiments, the second connection member 46 can have a protruding shoulder or tab feature, such as tabs 46b, to prevent separation, i.e., to prevent the second connection member 46 from being withdrawn through the split pivot element 56.

The first connection member 44 includes a cavity 58 for receiving the straight portion 46a of the second connection member 46 and for receiving the split pivot element 56. The cavity 58 includes a cylindrical cavity 58a into which the straight portion 46a of the second connection member 46 can translate. The cavity 58 also includes a spherical cavity 58b for receiving and supporting the split pivot element 56, thereby allowing for multi-axial movement of the second connection member 46 relative to the first connection member 44. The cavity 58 further includes openings 58c in opposing sides of the first connection member 44. The openings 58c allow portions of the straight portion 46a that extend beyond the split pivot element 56 and into the cylindrical cavity 58a to be moved more freely, thereby allowing the for an increased range of motion between the first and second connection members 44 and 46.

The collar 50 can include one or more tabs 50a for preventing the movement of the collar 50 from the locking position shown in FIG. 4B back to the unlocking position shown in FIG. 4A. The tabs 50a travel along respective guiding recesses 59a, which are formed along the first connection member 44. The tabs 50a reside on a distal end of a trailing resilient arm 50b, which urges the tabs 50a toward the first connection member 44. Thus, once the collar 50 is moved to the locking position shown in FIG. 4B, the tabs 50a snap into corresponding locking recesses 59b, thereby locking the position of the collar 50.

Figure 5:
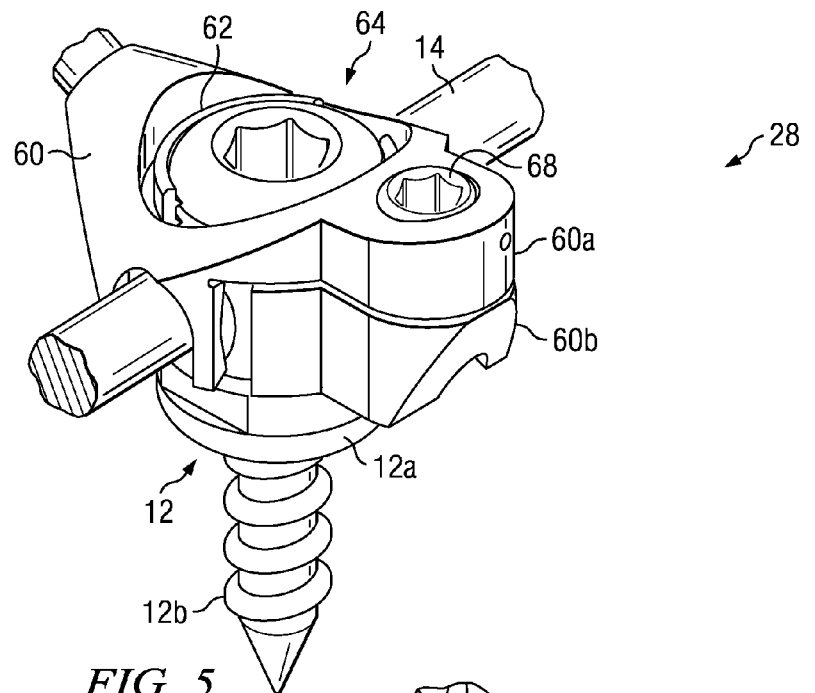
FIG. 5 shows a clamp, suitable for use with cross connecting devices disclosed herein, attached to a spinal fixation device as shown in FIGS. 1A and 1B.

Turning next to FIGS. 5-9, an exemplary clamp 28 is shown for connecting a cross connecting device, such as cross connecting device 20 or 40, to other components of the spinal fixation system 10, such as spinal fixation devices 12 and/or rods 14. The clamp 28 includes an outer housing 60 and an inner housing 62. The outer housing 60 supports the inner housing 62. The inner and outer housings 60 and 62 define a through-hole 64 receiving the body 12a of a spinal fixation device 12, as shown in FIG. 5. The outer housing 60 includes a fixed housing portion 60a and an adjustable housing portion 60b. The outer housing also defines a threaded cavity 66 for receiving a set screw 68, as most clearly shown in FIG. 8.

Figure 7A:
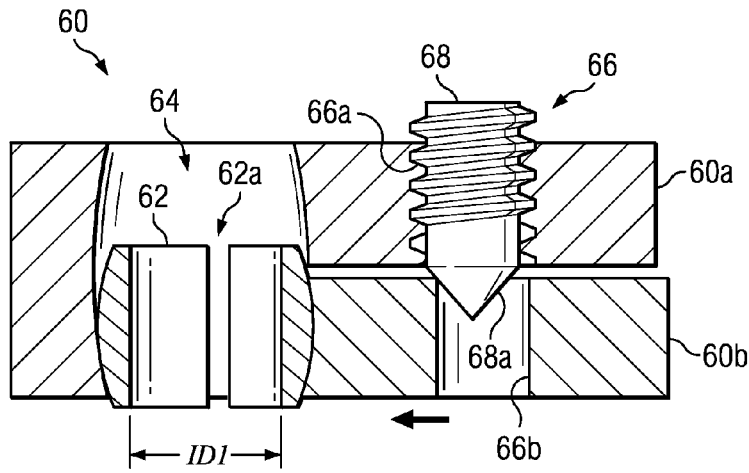
FIGS. 7A and 7B show simplified block diagrams of the clamp shown in FIGS. 5-6B.
Figure 7B:
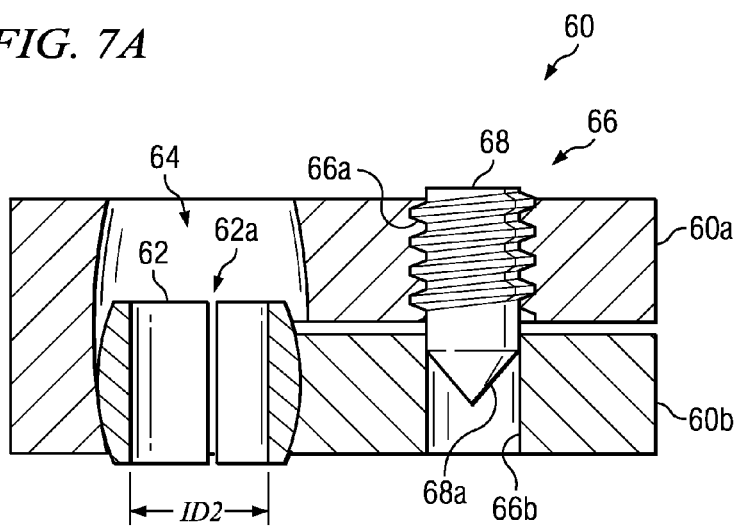
Figure 8:
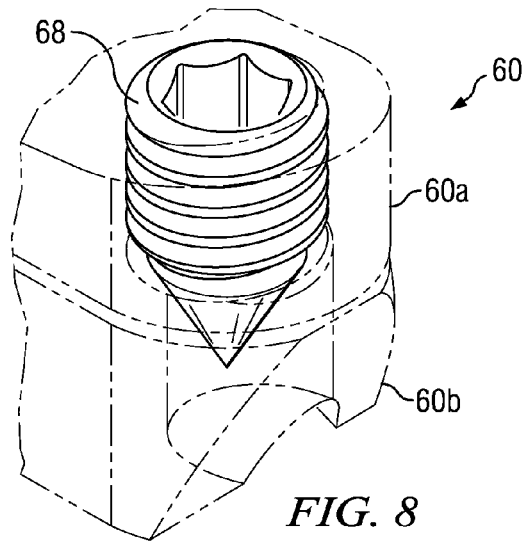
FIG. 8 shows an enlarged partial view of the clamp shown in FIGS. 5-7B, with the clamp body shown in phantom for better illustration of a set screw installation.

FIGS. 7A and 7B show schematic cross-sectional views of simplified block diagrams of the clamp 28. The views shown in FIGS. 7A and 7B have been simplified in order to allow for an improved understanding of the clamping action of the clamp 28. The clamping action of the clamp 28 occurs within the through-hole 64. The through-hole 64 has an inner diameter ID1 when relaxed, as shown in FIG. 7A. The inner diameter ID1 can be adjusted to a smaller inner diameter ID2, shown in FIG. 7B, for tightening the housings 60 and 62 onto the body 12a of a spinal fixation device 12.

The inner diameter can be adjusted from inner diameter ID1 to inner diameter ID2 by inserting and tightening the set screw 68. The threaded cavity 66 includes an upper cavity portion 66a and a lower cavity portion 66b. Initially, when the clamp 28 is relaxed as shown in FIG. 7A, the upper and lower cavity portions 66a and 66b are misaligned. The set screw 68 includes a conical end 68a that advances through the threaded cavity 66 as the set screw 68 is tightened. As the conical end 68a enters the lower cavity portion 66b, the set screw 68 urges the alignment of the upper and lower cavity portions 66a and 66b, thereby causing the inner diameter of the through-hole 64 to be reduced from inner diameter ID1 to inner diameter ID2. The inner diameter ID1 is large enough to allow the body 12a to easily enter the through-hole 64, while the inner diameter ID2 is small enough to compress the clamp onto the body 12a, thereby locking the body 12a within the through-hole 64.

The inner housing 62 can include one or more channels 62a that allow the inner housing 62 to be expanded and compressed. For example, the inner housing 62 can be compressed from having the inner diameter ID1 to having the inner diameter ID2. The outer housing 60 can also include one or more expansion/compression channels 60c, shown in FIG. 6A, that allow the outer housing 60 to be expanded and compressed. For example, the outer housing 60 can be compressed, thereby compressing the inner housing 62 from having the inner diameter ID1 to having the inner diameter ID2.

The channel 60c can include one or more transverse channel regions, such as transverse channel region 60d, for preventing the adjustable housing portion 60b from being urged directly away from the fixed housing portion 60a (downward in FIGS. 7A and 7B) as the set screw 68 is being driven into the lower cavity portion 66b.

Figure 6A:
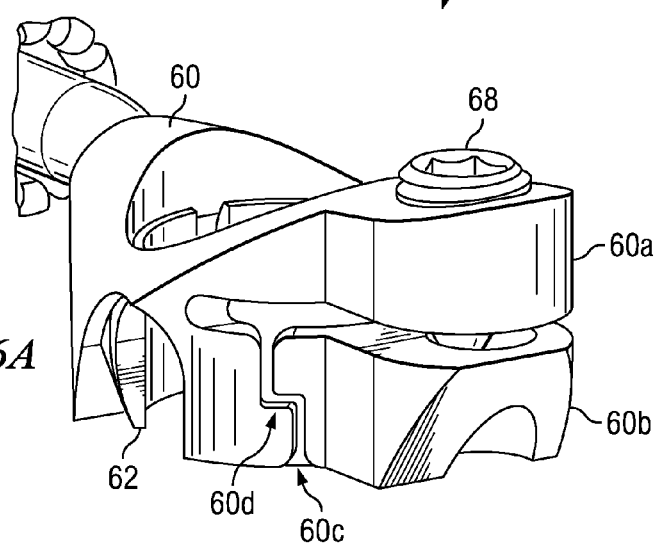
FIGS. 6A and 6B show opposing views of the clamp shown in FIG. 5 with the clamp in an unlocked configuration.
Figure 6B:
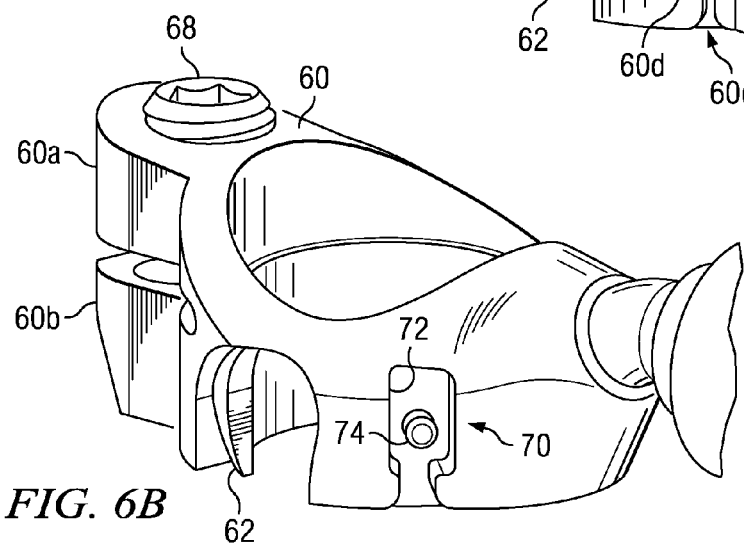

FIG. 5 shows the set screw 68 driven sufficiently for clamping the clamp 28 onto the body 12a of a spinal fixation device 12, corresponding to the view of the set screw 68 shown in FIG. 7B. FIGS. 6A and 6B show the set screw 68 installed only in the upper cavity portion 66a, corresponding to the view of the set screw 68 shown in FIG. 7A.

Figure 9A:
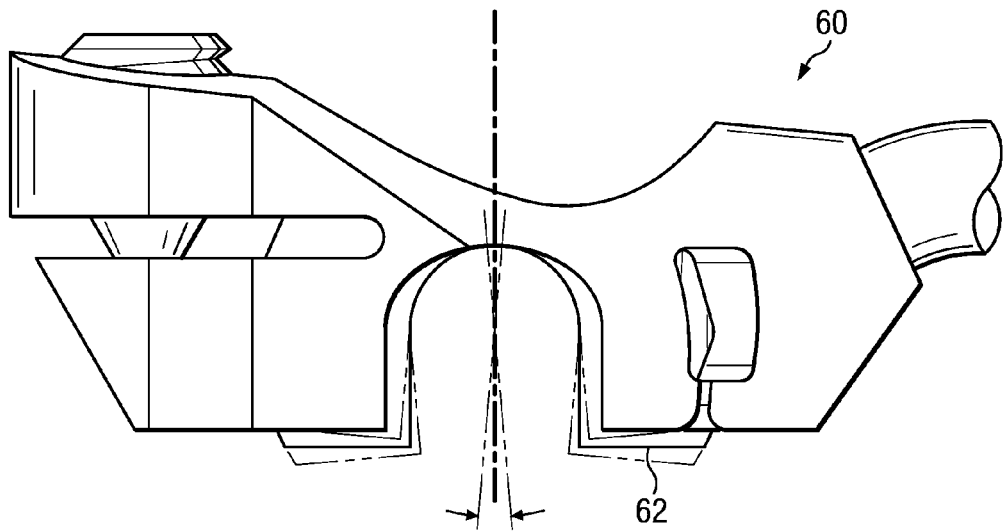
FIGS. 9A-9C show examples of angular adjustments that can be made within the clamp shown in FIGS. 5-8.
Figure 9B:
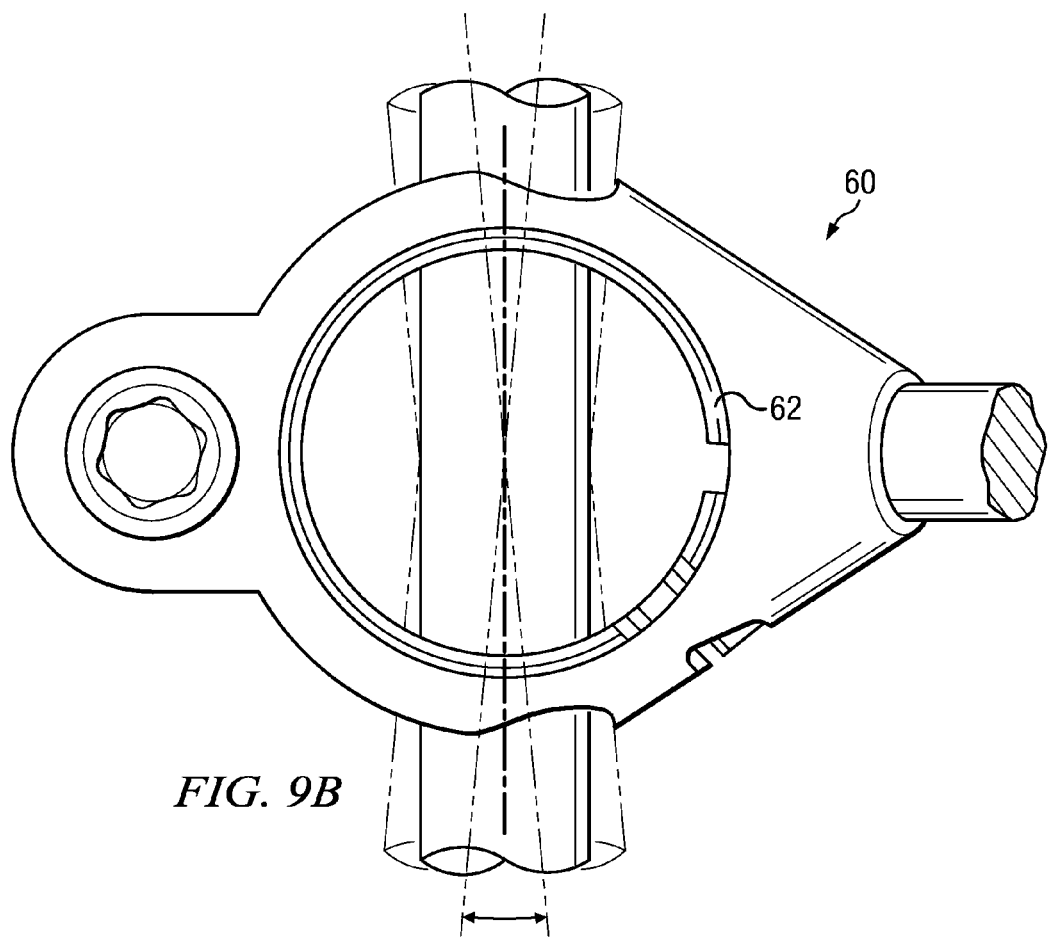
Figure 9C:
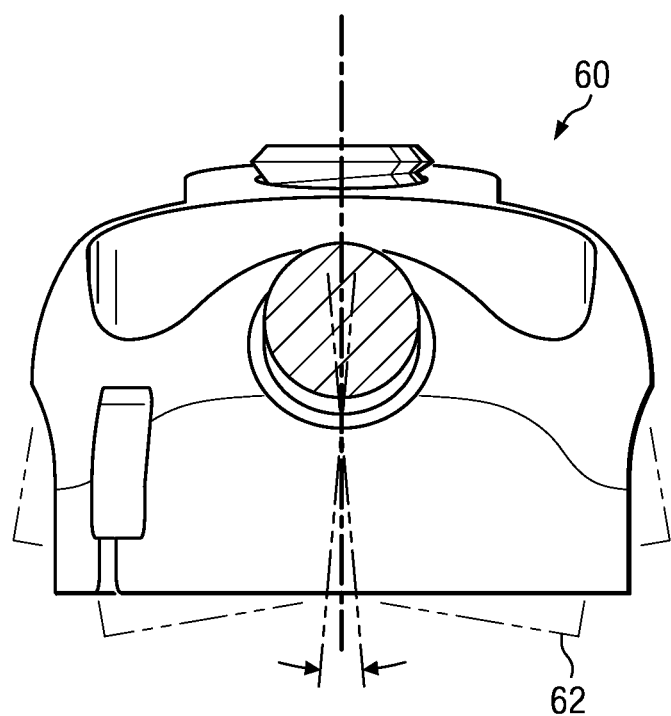

Turning next to FIGS. 9A-9C, the inner housing 62 can be repositioned relative to the outer housing 60 about at least three degrees of freedom while the clamp 28 is unlocked, i.e., the set screw 68 is not aligning the upper and lower cavity portions 66a and 66b. As shown in FIG. 9A, the inner housing 62 can be moved about a first axis such that the inner housing 62 can tilt relative to the outer housing 60; as shown in FIG. 9B, the inner housing 62 can be moved about a second axis such that the inner housing 62 can rotate relative to the outer housing 60; and as shown in FIG. 9C, the inner housing 62 can be moved about a third axis such that the inner housing can tilt relative to the outer housing 60.

The degree of movement of the inner housing 62 relative to the outer housing 60 can be limited by a limiter 70, which is best shown in FIG. 6B. The limiter 70 includes a limit window 72 and a limit pin 74. The limit window 72 is defined by the outer housing 60, while the limit pin 74 is fixed to the inner housing 62. The limit pin 74 can be, for example, a deformable tab that is machined into the inner housing 62. The size and shape of the limit window 72 can be selected based on the degree of movement desired between the inner housing 62 and outer housing 60.

Alternative clamps can be used with the cross connecting devices 20 and 40. For example, alternative embodiments for the clamp 28 can include embodiments described in U.S. provisional patent application Ser. No. 61/473,004, titled "CLAMP FOR SPINAL CROSS CONNECTING DEVICE," filed on Apr. 7, 2011, the disclosure of which is incorporated herein by reference in its entirety.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A cross connecting device suitable for connecting first and second spinal fixation devices, the cross connecting device comprising:
a fixable pivot junction, the pivot junction comprising a slidable collar and a pivotable joint that is pivotable about a pivot point, the collar being configured for fixating the pivot junction;
first and second connection members connected by the fixable pivot junction such that the fixable pivot junction allows the first and second connection members to be repositioned relative to each other; and
first and second clamps connected to respective ones of the first and second connection members at distal ends of the connection members relative to the fixable pivot junction;
wherein the pivotable joint comprises a tapered interface and a split pivot element;
wherein the tapered interface is configured for applying a compressive load to the split pivot element and the second connection member while the slidable collar is in the locking position; and
wherein the clamps each comprise an outer housing and an inner housing rotationally or angularly adjustable relative to each other.

2. The cross connecting device of claim 1, wherein the collar is slidable between an unlocking position and a locking position.

3. The cross connecting device of claim 2, wherein the locking position is closer to a pivot point of the pivotable joint than the unlocking position.

4. The cross connecting device of claim 2, wherein the collar further comprises one or more tabs for preventing the movement of the collar from the locking position to the unlocking position.

5. The cross connecting device of claim 1, wherein the tapered interface is connected to the first connection member.

6. The cross connecting device of claim 1, wherein the tapered interface comprises plurality of slits surrounding the split pivot element.

7. The cross connecting device of claim 1, wherein the first and second clamps are configured to be connected to respective ones of the first and second spinal fixation devices.

8. The cross connecting device of claim 7, wherein each of the first and second clamps includes a respective locking member that can be adjusted to tighten the respective clamp onto the respective spinal fixation device.

9. The cross connecting device of claim 8, wherein the clamps each include a socket for receiving a respective one of the set screws, where the socket includes a top hole and a bottom hole, the bottom hole being misaligned with the top hole.

10. The cross connecting device of claim 9, wherein each of the set screws includes a tapered end, wherein the tapered end of the set screw can pass through the misaligned bottom hole as the set screw is driven into the socket, thereby urging the misaligned bottom hole to align with the top hole as the set screw is driven into the socket.

11. The cross connecting device of claim 9, wherein the clamp tightens onto the respective spinal fixation device as the misaligned bottom hole is aligned with the top hole by the set screw.

12. The cross connecting device of claim 1, wherein the outer housing and the inner housing are rotationally and angularly adjustable relative to each other along at least two degrees of freedom.

13. The cross connecting device of claim 1, wherein the outer housing includes a channel that allows for expansion and compression of the outer housing.

14. The cross connecting device of claim 13, wherein the channel includes a transverse channel region.

15. The cross connecting device of claim 1, wherein the inner housing includes a channel that allows for expansion and compression of the inner housing.

16. The cross connecting device of claim 1, wherein the fixable pivot junction allows the first and second connection members to be translationally, rotationally, and angularly repositioned relative to each other.

* * * * *